United States Patent [19]

Holaday et al.

[11] 4,267,182

[45] May 12, 1981

[54] NARCOTIC ANTAGONISTS IN THE THERAPY OF SHOCK

[75] Inventors: John W. Holaday, Rockville, Md.; Alan I. Faden, Washington, D.C.

[73] Assignee: The United States of America as represented by the Secretary of the Army, Washington, D.C.

[21] Appl. No.: 3,699

[22] Filed: Jan. 16, 1979

[51] Int. Cl.³ .................................................. A01N 43/42
[52] U.S. Cl. ........................................ 424/260; 424/95
[58] Field of Search ............................................ 424/260

[56] References Cited

U.S. PATENT DOCUMENTS

| | | | |
|---|---|---|---|
| 2,364,833 | 12/1944 | Weijlard et al. | 546/44 |
| 2,891,954 | 6/1959 | Weijlard | 546/44 |
| 3,148,118 | 9/1964 | Thesing et al. | 424/260 X |
| 3,214,341 | 10/1965 | Feinstone | 424/260 X |
| 3,254,088 | 5/1966 | Lewenstein et al. | 546/45 |
| 3,717,643 | 2/1973 | Archer | 424/260 X |
| 3,823,234 | 7/1974 | Mauvernay | 424/260 |
| 4,001,247 | 1/1977 | Zimmerman et al. | 424/258 X |
| 4,035,511 | 7/1977 | Messing et al. | 424/260 X |
| 4,042,682 | 8/1977 | Spector | 424/260 |

OTHER PUBLICATIONS

M. Woods et al., The Physiologist, 8/31/78, vol. 21, p. 129.
Chem. Abs., 1978, vol. 88, pp. 69112x, 32035y.
Chem. Abs., 1976, vol. 85, p. 171810y.
Chem. Abs., 1977, vol. 86, pp. 12304r.
Merck Manual, 11th Edition, 1/1967, pp. 154–159, 1538–1540 & 1547.

*Primary Examiner*—Dale R. Ore
*Attorney, Agent, or Firm*—William G. Gapcynski; Werten F. W. Bellamy; Sherman D. Winters

[57] ABSTRACT

The use of narcotic antagonists (e.g., naloxone) in shock therapy is disclosed.

16 Claims, No Drawings

NARCOTIC ANTAGONISTS IN THE THERAPY OF SHOCK

BACKGROUND OF THE INVENTION

The field of invention relates to the therapy of shock, which is defined in Blakiston's New Gould Medical Dictionary, 2d ed., page 1092 (McGraw - Hill, N.Y., 1956) as follows: "The clinical manifestations of an inadequate volume of circulating blood accompanied by physiologic adjustments of the organism to a progressive discrepancy between the capacity of the arterial tree and the volume of blood to fill it." A primary characteristic of shock is hypotension. Current attempts at treatment involve the administration of isoosmotic fluids such as blood, plasma, or volume expanders (e.g., albumin) in conjunction with vasoactive agents such as dopamine. However, such attempts are often ineffective, because they are aimed at treating the effects of shock (inadequate perfusion) instead of its causes. There are serious drawbacks associated with such attempts: (1) time is required for blood typing and/or setting up intravenous systems for administering blood or other isoosmotic fluids; (2) blood pressure must be constantly monitored when vasoactive agents such as dopamine are administered; (3) current treatments can be administered only in a clinical environment, and potential life-threatening time delays usually occur between diagnosis and treatment; and (4) moreover, such attempts are not always successful in the management of shock syndromes.

SUMMARY OF THE INVENTION

Accordingly, there is a need for an improved method of shock therapy. It is an object of this invention to provide such a method.

Another object of the invention is to treat shock at a causal level, instead of attempting to treat only the effects of shock.

Another object of the invention is to provide a treatment of shock which may be administered rapidly, thus eliminating the potentially life-threatening time delays now required.

Another object of the invention is to provide a method of treating shock without the need to monitor blood pressure continuously.

Another object of the invention is to treat shock with a known class of drugs.

Yet another object of the invention is to provide a pretreatment for animals with inadequate adrenal function, in order to protect them from their hypersensitivity to shock states, preceding surgery or other anticipated trauma.

Still other objects of this invention will become apparent to those of ordinary skill in the art upon reading this disclosure.

The above objects are achieved by the improved method of shock therapy of this invention, which embraces: (1) a method of treating an animal which is suffering from shock by administering to said animal a therapeutically effective amount of a drug selected from the group consisting of narcotic antagonists and the pharmaceutically-acceptable acid addition salts thereof; and (2) a method of pretreating an animal in order to protect it from shock by administering to said animal a therapeutically effective amount of a drug selected from the group consisting of narcotic antagonists and the pharmaceutically-acceptable acid addition salts thereof.

The term "animal" in this disclosure refers to any organism which is capable of suffering from shock.

It is believed that narcotic antagonists and their pharmaceutically-acceptable acid addition salts possess therapeutic value for treating all forms of shock, inclusive of but not restricted to the following forms:
anaphylactic
anaphylactoid
burn
cardiogenic
hematogenic (hemorrhagic, wound, hypovolemic)
nervous
neurogenic (fainting)
restraint
septic (vasogenic, endotoxic)
spinal
traumatic Moreover, the classification of a drug as a pure narcotic antagonist or partial antagonist warrants its inclusion in this invention for use in shock therapy. Pure antagonists such as naloxone are included, as well as other drugs which possess varying degrees of morphine-like or agonist activity together with their antagonist activity. The invention includes, but is not restricted to, the following narcotic antagonists:
naloxone
naltrexone
nalorphine
diprenorphine
lavallorphan
pentazocine
metazocine
cyclazocine
etazocine
peptide drugs with antagonistic activity Also, any drug with demonstrable agonist activity can be imparted with antagonist activity by the addition of an aliphatic group to its nitrogen moiety (e.g., nalorphine is N-allylnormorphine), and the use of such drugs is included within the scope of this invention.

The use of pharmaceutically-acceptable acid addition salts of narcotic antagonists is also within the scope of the invention. In general, any suitable inorganic or organic acid may be used to prepare such salts. Non-limiting examples of suitable inorganic acids are hydrochloric, hydrobromic, sulfuric, nitric, phosphoric, phosphorous, and perchloric acids. Non-limiting examples of suitable organic acids are tartaric, citric, acetic, succinic, maleic, malic, fumaric, oxalic, ascorbic, benzoic, lactic, palmitic, pamoic, lauric, stearic, oleic, myristic, lauryl sulfuric, linoleic, and linolenic acids.

Whether treating an animal for shock or pretreating it in order to protect it from shock, any suitable route of administration may be used depending on the particular drug administered. For example, one of ordinary skill can select from the intravenous, intramuscular, subcutaneous, parenteral, oral, and intrathecal routes of administration. The dose of drug contemplated is, broadly, a therapeutically effective amount; a preferred range is about 0.01 mg per kg to about 10 mg per kg body weight of animal.

EXPERIMENTAL DETAILS

The following description provides the salient features of laboratory tests which lead to the conclusion that narcotic antagonists and their pharmaceutically-acceptable acid addition salts are useful in the therapy of shock. However, applicants do not wish to be limited by the particular experimental details which were used in conducting these tests.

Initially, the endotoxin model of septic shock was chosen for testing. Male Wistar rats (Walter Reed strain) weighing 275–300 g were prepared with two indwelling cannulae, one in the tail artery for blood pressure monitoring and the other in the external jugular vein for drug administration. From 1–2 days after surgery, these conscious and alert rats were injected intravenously with 4 mg *Escherichia coli lipopolysaccharide endotoxin. This injection of endotoxin usually produced a rapid fall in blood pressure, from an average mean arterial pressure (MAP) of* 95 mm Hg to an MAP of 65–70 mm Hg, within 15 min. When MAP dropped to this low value, naloxone hydrochloride was injected intravenously at a dosage of 10 mg per kg in one half of the rats; the other half received placebo (saline) injections. The rats which received naloxone experienced a return of blood pressure to within normal ranges within 5 seconds, whereas placebo-injected rats experienced no increase in blood pressure. This striking difference between naloxone-treated and saline-control rats was confirmed in separate studies using 9–10 rats per group. Naloxone in the absence of endotoxin, however, was without effect on MAP. For further experimental details and results, the reader is referred to J. W. Holaday et al., Nature 275:450–51 (Oct. 5, 1978).

Studies in the rat-endotoxin shock model were expanded to assess the effect of different doses of naloxone on MAP. In these tests, the rats were injected intravenously with 40 mg per kg *Escherichia coli* lipopolysaccharide endotoxin. Three doses of naloxone hydrochloride (0.1 mg per kg; 1.0 mg per kg; and 10.0 mg per kg) were chosen, and all doses successfully reversed endotoxin-induced hypotension in contrast to saline. Survival at 24 hrs was also monitored. Naloxone had no apparent effect on rat survival, although naloxone-injected rats were normotensive or hypertensive at death while saline-control rats were significantly hypotensive. This suggests that factors other than blood pressure maintenance are determinants of survival after endotoxin administration in the rat. However, the more precipitous the fall in blood pressure following endotoxin, the more rapid and complete its reversal by naloxone injections.

In addition to the endotoxin model of septic shock in rats, the efficacy of naloxone hydrochloride in reversing the hypotension produced by hypovolemic shock was tested. Conscious rats were partially exsanguinated through the intravenous cannulae while blood pressure was again monitored through the tail artery cannula. Approximately one half of the estimated total blood volume was removed. In a 250–300 g rat, this amounted to 9–10 ml blood, removed as needed to maintain an MAP of 35–40 mm Hg over 20 min. Either naloxone hydrochloride (1.0 mg per kg) or saline was then administered intravenously, and blood pressure was monitored for an additional 2 hrs. Survival over 24 hrs was also determined. Based on results in 30 rats, naloxone significantly improved blood pressure in this model of hypovolemic shock. Furthermore, 24 hr survival was also affected, since 7/15 saline-control rats died and only 2/15 of the naloxone-treated rats died.

Tests on the efficacy of naloxone in reversing the hypotension produced by rapid severing of the cervical spinal cord in the cat and rat have also been performed. In these studies, naloxone restored MAP toward normal values in doses between 0.1 mg per kg and 10 mg per kg in two cats and 30 rats. Therefore, in this model of spinal shock, once again naloxone improved MAP significantly.

Finally, studies have been conducted with dogs in both the endotoxic and hypovolemic shock models. In both models, naloxone-treated dogs showed improvement in all essential cardiovascular indices, including mean arterial pressure, systolic arterial blood pressure, diastolic arterial blood pressure, cardiac output, cardiac contractility, and heart rate. Moreover, survival was significantly improved in both models by naloxone treatment.

DISCUSSION

The successful test results in connection with various shock forms provide ample evidence that the specific opiate antagonist naloxone is efficacious for the treatment of shock, regardless how induced. Without being bound by any theory, it seems likely that endogenous opiates (endorphins) are released during shock states and that they contribute to hypotension, which is a primary characteristic of shock. See J. W. Holaday et al. supra. The antagonist naloxone significantly reverses this hypotension. Accordingly, there is rational basis to believe that narcotic antagonists in general have direct therapeutic value in treating the various forms of shock. Narcotic antagonists appear to treat shock-hypotension at a causal level, because they block the hypotensive effects of the body's own substances which contribute to this pathophysiological state.

Among the narcotic antagonists, naloxone is a preferred drug for use in shock therapy because it increases blood pressure toward normal values within seconds after administration. Since naloxone is without effect on blood pressure in normal animals, the risk of over-correcting and causing hypertension or related effects by overdosage is minimal. Moreover, naloxone is currently available as a treatment for narcotic overdosages in humans.

We claim:

1. A method of treating an animal which is suffering from a form of shock selected from the group consisting of anaphylactic, anaphylactoid, burn, cardiogenic, hypovolemic, and septic which comprises administering to said animal a therapeutically effective amount of a narcotic antagonist drug selected from the group consisting of naloxone, naltrexone, nalorphine, diprenorphine, levallorphan, pentazocine, metazocine, cyclazocine, etazocine and the pharmaceutically-acceptable acid addition salts thereof.

2. The method of claim 1 wherein the animal is suffering from a form of shock selected from the group consisting of anaphylactic, anaphylactoid, burn, cardiogenic, hypovolemic, and septic.

3. The method of claim 1 wherein the animal is suffering from septic shock.

4. The method of claim 1 wherein the animal is suffering from hypovolemic shock.

5. The method of claim 1 wherein the drug is selected from the group consisting of naloxone and the pharmaceutically-acceptable acid addition salts thereof.

6. The method of claim 5 wherein the drug is naloxone hydrochloride.

7. The method of claim 3 wherein the drug is naloxone hydrochloride.

8. The method of claim 4 wherein the drug is naloxone hydrochloride.

9. A method of pretreating an animal in need thereof from a form of shock selected from the group consisting of anaphylactic, anaphylactoid, burn, cardiogenic, hypovolemic, and septic which comprises administering to said animal a therapeutically effective shock preventing amount of a narcotic antagonist drug selected from the group consisting of naloxone, naltrexone, nalorphine, diprenorphine, levallorphan, pentazocine, metazocine, cyclazocine, etazocine and the pharmaceutically-acceptable acid addition salts thereof.

10. The method of claim 9 wherein the animal is protected from a form of shock selected from the group consisting of anaphylactic, anaphylactoid, burn, cardiogenic hypovolemic, and septic.

11. The method of claim 9 wherein the animal is protected from septic shock.

12. The method of claim 9 wherein the animal is protected from hypovolemic shock.

13. The method of claim 9 wherein the drug is selected from the group consisting of naloxone and the pharmaceutically-acceptable acid addition salts thereof.

14. The method of claim 13 wherein the drug is naloxone hydrochloride.

15. The method of claim 11 wherein the drug is naloxone hydrochloride.

16. The method of claim 12 wherein the drug is naloxone hydrochloride.

* * * * *